United States Patent [19]
Fenton, Jr. et al.

[11] Patent Number: 5,112,301
[45] Date of Patent: May 12, 1992

[54] BIDIRECTIONAL CHECK VALVE CATHETER

[75] Inventors: Paul V. Fenton, Jr., Marblehead, Mass.; Thomas M. Young, Traverse City, Mich.; William J. Gorman, Newburyport, Mass.

[73] Assignee: Strato Medical Corporation, Beverly, Mass.

[21] Appl. No.: 717,618

[22] Filed: Jun. 19, 1991

[51] Int. Cl.$^5$ ................................................ A61H 1/00
[52] U.S. Cl. ........................................ 604/30; 604/247
[58] Field of Search ................ 604/30, 31, 34, 35, 604/169, 246, 247, 93, 119, 320; 137/493, 493.7; 251/343, 344

[56] References Cited

U.S. PATENT DOCUMENTS

| | | | |
|---|---|---|---|
| 3,995,617 | 12/1976 | Watkins et al. | 128/1 D |
| 4,246,932 | 1/1981 | Raines | 604/30 |
| 4,657,536 | 4/1987 | Dorman | 604/247 |
| 4,671,796 | 6/1987 | Grashong et al. | 604/247 |
| 4,705,501 | 11/1987 | Wigness et al. | 604/43 |
| 4,725,266 | 2/1988 | Siposs | 604/247 |
| 4,857,054 | 8/1989 | Helfer | 604/102 |
| 4,973,319 | 11/1990 | Melsky | 604/247 |

FOREIGN PATENT DOCUMENTS 9009204 8/1990 World Int. Prop. O. .

*Primary Examiner*—Cary E. O'Connor
*Attorney, Agent, or Firm*—Lahive & Cockfield

[57] ABSTRACT

A valved catheter is disclosed having an elongated, flexible tubular element defining a lumen extending along an axis substantially parallel to the central axis of the tubular element, and a bidirectional check valve assembly near its distal end which controls fluid flow in the tubular element. The valve assembly includes an aspiration valve offset from the tip of the distal end and an infusion valve formed at the tip of the distal end. The aspiration valve is generally defined by port(s) in the tubular element and a sleeve within the element underlying the ports, where the sleeve normally closes the ports. The aspiration valve permits fluid flow from the bloodstream into the element when the static fluid pressure inside the distal end is lower than the static fluid pressure outside the aspiration valve by an amount sufficient to displace the sleeve to allow fluid flow through the ports. The infusion valve includes a throat formed in the distal end which tapers down to a mouth formed by jaws at the tip. The mouth is essentially closed to fluid inflow from the patient into the tubular element and normally closed to fluid outflow from the tubular element into the patient. The infusion valve permits fluid infusion into the bloodstream when the static fluid pressure inside of the tubular element sidtal end is higher than the static fluid pressure outside of the infusion valve by an amount sufficient to force the mouth open. A bidirectionally valved multiple lumen catheter is also disclosed.

12 Claims, 4 Drawing Sheets

BIDIRECTIONAL CHECK VALVE CATHETER

BACKGROUND OF THE INVENTION

The present invention relates to a catheter intended for at least partial implantation within a living body for special or long term usage, and more particularly to a catheter having a bidirectional check valve for controlling fluid flow into and out of the catheter.

Various medical procedures require vascular access over a period of time. Such procedures may include implantation of a permanent intravascular device for use with portable drug infusion devices, for hemodialysis, or for cases where continuous blood work or access to the bloodstream is required. These procedures are often performed by using either transcutaneous or totally implanted catheters.

It is desirable to limit the number of such devices intruding into the human body and it is also desirable to limit the possibility of infection, blood embolism and the like, by precluding diffusion of blood into the device when it is not in use.

A commercially available catheter features a slit-type bidirectional check valve. The tip of the catheter is closed and the side wall of the catheter near the tip is slit, to form the slit valve. The valve allows both aspiration of blood and infusion of fluids. The check valve precludes the diffusion of blood into the lumen when the catheter is not in use. A catheter of this type is known as the Groshong catheter (available from Catheter Technology Corporation, Salt Lake City, Utah).

While various other valved catheters are also known, there is still a need for an improved at least partially implantable, bidirectional check valve catheter assembly which is easy to manufacture and easy to install in a patient, and yet limits the possibility of infection, blood embolism and the like.

It is therefore an object of the present invention to provide an implantable catheter which is easy to manufacture.

It is another object of the present invention to provide an intravascular catheter with a bidirectional check valve which permits long term placement in the bloodstream.

It is a further object of the present invention to provide a multi-lumen intravascular catheter in which each lumen includes a bidirectional check valve.

SUMMARY OF THE INVENTION

The present invention provides an improved bidirectional check valve catheter which is easy to manufacture, installs easily and permits long term placement in the patient's bloodstream. In one aspect of the invention, a valved catheter includes a valve assembly adapted for bidirectional flow of fluid between the proximal and distal ends of the catheter, but which prevents diffusion of blood into the catheter when it is not in use.

In an illustrative embodiment of the invention, a bidirectionally valved catheter includes an elongated, flexible tubular element which extends along a central axis, and defines a lumen extending along that central axis from a proximal end to a distal end. A valve assembly is formed at the distal end in cooperation with the tubular element. The assembly includes an aspiration valve for permitting fluid flow from outside to inside of the tubular element for aspiration of blood from the patient's bloodstream and an infusion valve for permitting fluid flow from inside to outside of the tubular element for delivery of fluid into the patient's bloodstream.

The aspiration valve is a sleeve valve including one or more inflow ports extending between the exterior and interior surfaces of the tubular element. A flexible tubular sleeve is disposed adjacent to the inner surface of the portions of the tubular element that include the inflow ports. The valve action is formed by the sleeve, which is nominally urged against the interior surface of the tubular element in a manner which normally prevents fluid inflow and essentially prevents fluid outflow through the inflow ports. A portion of the sleeve is displaceable to permit fluid inflow when the static fluid pressure outside of the ports is higher than the static fluid pressure inside the tubular element by an amount sufficient to force a portion of the sleeve away from the interior surface of the tubular element.

The infusion valve is a slit valve and in one form of the invention includes a normally closed "duck bill"-type valve at the distal tip of the tubular element. This duck-bill valve is essentially closed to fluid inflow and normally closed to fluid outflow, although in response to conditions where the static fluid pressure within the tubular element exceeds the static fluid Pressure outside that portion of the catheter (by a sufficient amount), then the infusion valve permits outflow of fluid.

In a preferred embodiment of the invention, the tubular element is open at its distal end, and the infusion valve is formed by the abovesaid sleeve which extends from the aspiration valve all the way to the tip of the distal end of the tubular element. The sleeve exterior surface is generally conformed to, and nominally urged against, the internal contour of the tubular element. However, at the tubular element distal end, the end of the sleeve tapers down to form the abovesaid infusion valve. More particularly, the sleeve is formed so that its end establishes a closed slit when there is little or no static pressure differential at the distal tip of the catheter. The opposed portions of the sleeve that form the slit are forced away from each other to open the infusion valve by relative elevation of pressure within the catheter. Hence the infusion valve facilitates fluid outflow when the static fluid pressure inside of the tubular element is higher than the static fluid pressure outside of the tubular element by an amount sufficient to displace the opposed portions of the sleeve that form the slit. In alternate embodiments, for example, the infusion valve may be formed directly in the tubular element.

To establish a multiple lumen catheter, two or more of the above described bidirectional valve catheters can be coupled together along the sidewalls of their respective tubular elements.

BRIEF DESCRIPTION OF THE DRAWINGS

These and other advantages of the present invention will be more fully understood by reference to the following detailed description in conjunction with the attached drawings in which.

DETAILED DESCRIPTION OF THE PREFERRED EMBODIMENT

Figure 1:
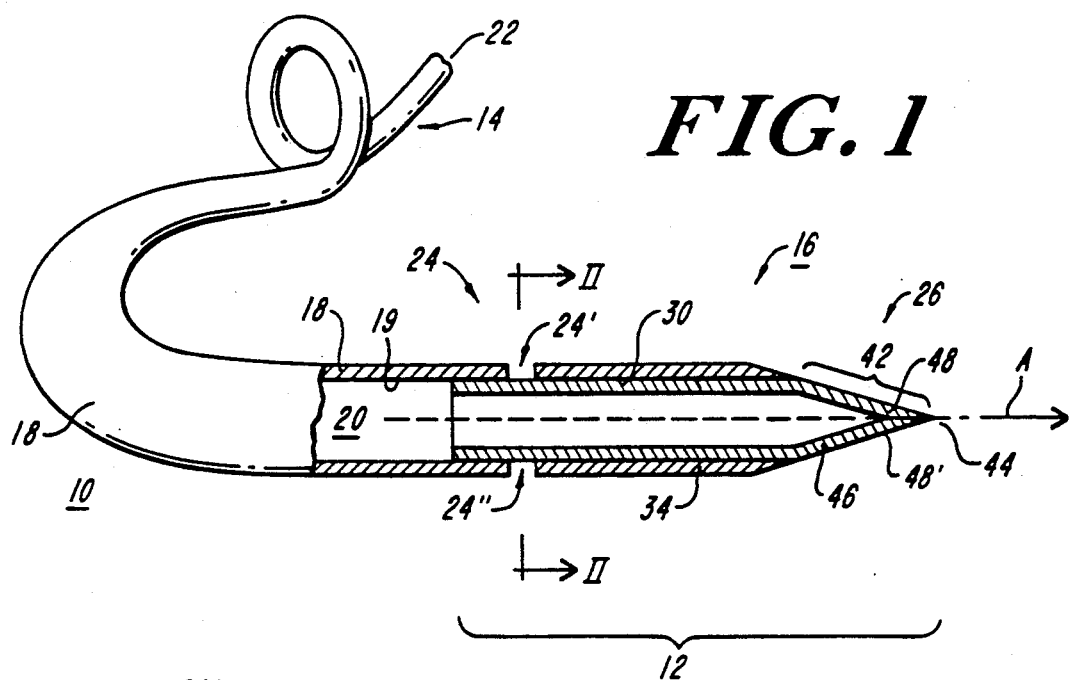
FIG. 1 shows, partially in cross-section and partially in perspective, a catheter in accordance with the present invention.
Figure 4:
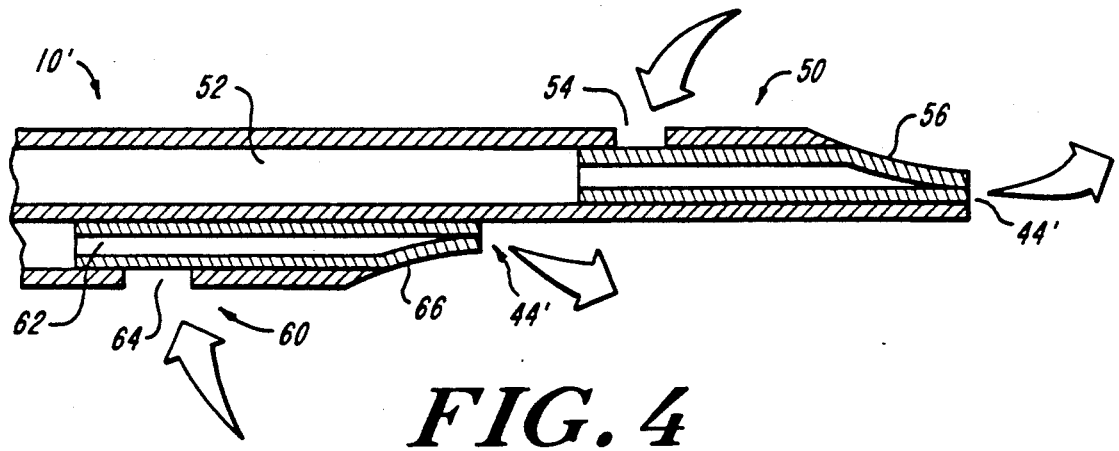
FIG. 4 is a side cross-section of a preferred dual lumen embodiment of the present invention.
Figure 5:
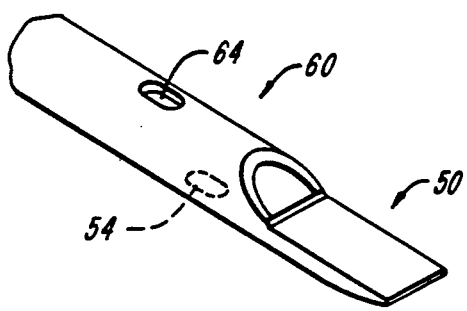
FIG. 5 is a perspective view of the device of FIG. 4.

A single lumen, bidirectional valved catheter embodying the invention is shown in FIG. 1 in which a flexible tubular element, such as a catheter 10, defines an elongate wall member 18, whose interior surface 19 defines a central lumen 20 extending along a central axis A. The catheter is preferably formed of biocompatible material such as silicone or polyurethane. In the embodiment of FIG. 1, the cross-section of lumen 20 is circular but other shapes may also be used. For example, a "D" shaped cross-section is particularly useful for a dual lumen embodiment, as shown in FIGS. 4 and 5. The catheter has a first or proximal end 14 and a second or distal end 16. The catheter 10 is adapted for placement of the distal end 16 in a patient's vascular system while the proximal end is outside the patient. With this configuration, inflow (infusion) of fluid may selectively be established from proximal end 14 to distal end 16 and into a patient's bloodstream, and outflow (aspiration) of fluid from the patient's bloodstream may selectively be established from distal end 16 to proximal end 14. Central lumen 20 terminates at the catheter proximal end 14 with a conventional coupling device at 22 to facilitate coupling the catheter proximal end to a syringe or other extra corporeal equipment or, alternatively, to an implanted fluid access port, for example.

A bidirectional check valve assembly 12 is formed in catheter distal end 16. Check valve assembly 12 includes an aspiration valve 24 and an infusion valve 26. As described more fully below, fluid infusion may be implemented under "positive" pressure from a device, such as a syringe, and fluid aspiration may be implemented under "negative" pressure such as may be generated by a syringe. As used herein, "positive" pressure refers to conditions where the static pressure in lumen 20 near distal end 16 exceeds the static pressure external to distal end 16. Similarly, "negative" pressure refers to conditions where the static pressure external to distal end 16 exceeds the static pressure in lumen 20 near the distal end 16.

Aspiration valve 24 includes ports 24' and 24". Ports 24' and 24" are generally circular holes extending through wall member 18. Two ports are shown in FIG. 1, however use of a plurality of ports, or even a single port, is also within the scope of the invention.

Figure 2A:
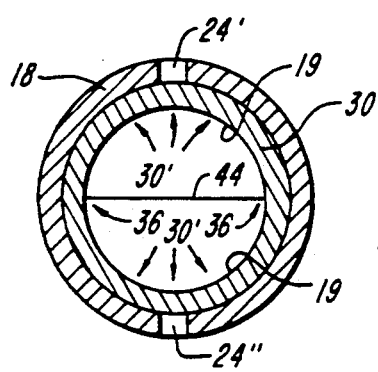
FIGS. 2A, 2B and 2C show radial cross-section views of the inflow valve assembly of FIG. 1 taken along line II-II for different operating conditions.
Figure 2B:
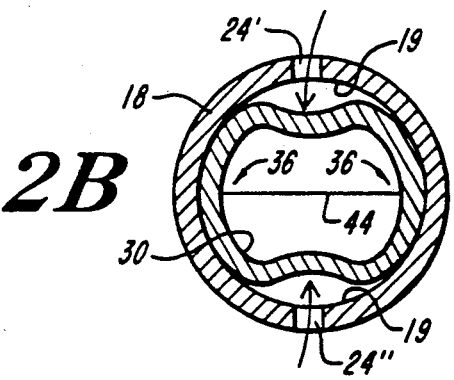

Ports 24' and 24" open out to the exterior of the catheter without obstruction but are interrupted as they open into catheter lumen 20 by a local portion of a flexible, tubular valve sleeve 30. The outer diameter of sleeve 30 substantially matches the inner diameter of wall member 18, so that the sleeve nominally is urged against the portions of the wall member 16 that includes the ports 24' and 24". Sleeve 30 is preferably formed of a resilient material, such as silicone or polyurethane, and, as shown in the radial cross-section of FIGS. 2A and 2B, is fixedly mounted at separate opposed regions 36 along its exterior to the interior of catheter wall member 18, such as by silicone. In the preferred embodiment, the entire outer periphery of sleeve 30 is joined to the interior surface of member 18 at a point between the section line II—II of FIG. 1 and the distal tip of the catheter.

In a neutral (or nominal) condition, where little or no pressure differential exists across the wall member 18, as shown in FIG. 2A, sleeve 30 normally closes aspiration valve 24 to fluid inflow (into lumen 20 from the patient) and effectively closes valve 24 to fluid outflow (from lumen 20 into the patient). Fluid inflow into lumen 20 is permitted when the fluid pressure outside valve 24 is higher than the pressure inside lumen 20 by an amount sufficient to force the unaffixed portions 30' of sleeve 30 partially away from the interior wall 19 of the catheter, as shown in FIG. 2B, thus permitting fluid aspiration from the patient's bloodstream into the lumen 20.

Infusion valve 26 includes an end section 34 of the catheter, and an end section 46 of the sleeve 30 which extends from the aspiration valve to the distal tip of catheter 10. The entire exterior of the portion of sleeve end section 46 that is adjacent to the inner surfaces 19 of wall member 18 is bonded to that inner surface in catheter end section 34. The end section 46 of the sleeve 30 forms a "duck-billed" valve including a throat 42 extending along the catheter central axis A from the aspiration valve which tapers down to a slit (or mouth) 44, which is essentially closed to fluid inflow and normally closed to fluid outflow. While the term "jaw" has been used herein to describe the opposed portion of the duck-billed valve, it will be understood that in the preferred embodiment, these elements are flexible and the opposed portions defining the slit may be described as "lips".

Figure 2C:
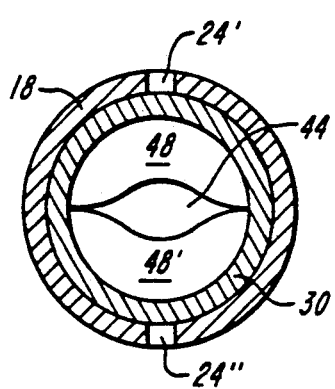

In its tapered section, throat 42 defines an upper jaw 48 and a lower jaw 48' which terminate at the slit (mouth) 44 at the tip of catheter 10. The jaws (or "lips") 48 and 48' are displaceable (in response to relatively high pressure inside lumen 20) in opposite directions to open mouth 44 to fluid flow, as shown in FIG. 2C. This arrangement permits fluid infusion to the patient when the fluid pressure inside of the catheter is higher than the fluid pressure outside of the catheter by an amount sufficient to displace jaws (or "lips") 48 and 48', thus opening mouth 44.

Figure 3A:
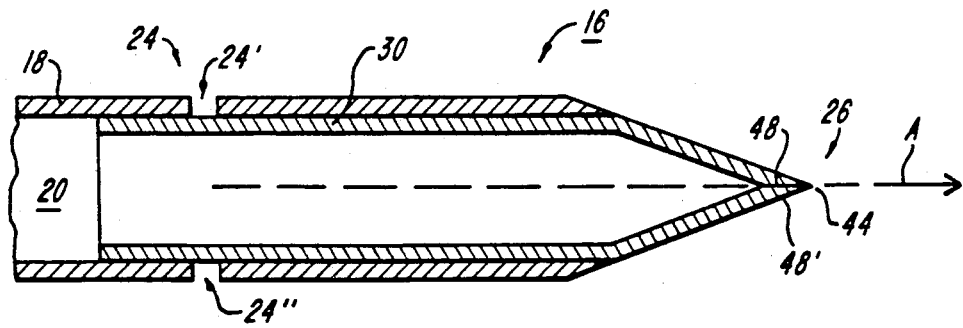
FIGS. 3A, 3B and 3C show axial cross-section views illustrating the operation of the bidirectional check valve of the embodiment of FIG. 1.
Figure 3B:
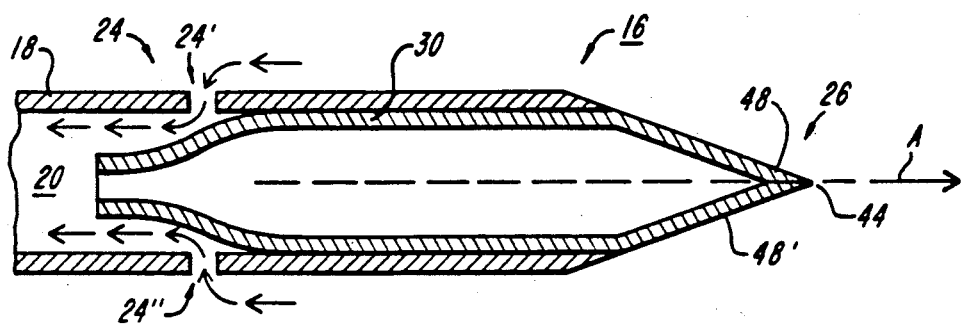
Figure 3C:
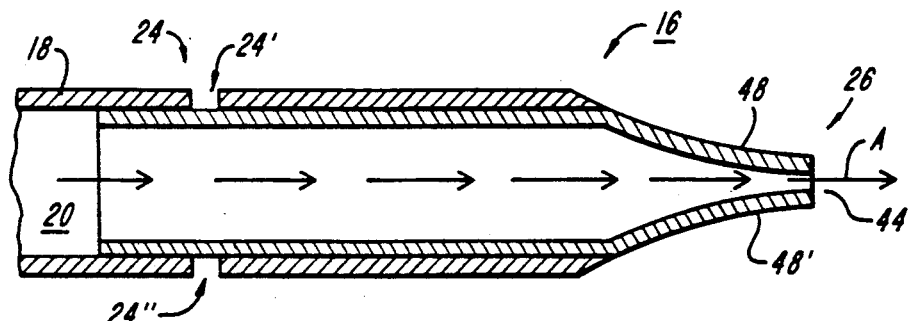

FIGS. 3A, 3B and 3C illustrate (for a two inflow port embodiment) the operations of the aspiration and infusion valves for conditions where there is little or no pressure differential between lumen 20 and regions exterior to the distal tip 16 (FIG. 3A), where there is a relatively high pressure exterior to tip 16 (FIG. 3B) and where there is a relatively low pressure exterior to tip 16 (FIG. 3C). In FIG. 3A, there is substantially no fluid flow; in FIG. 3B there is fluid flow (indicated by the arrows) into lumen 20; and in FIG. 3C there is fluid flow (indicated by the arrows) out of the distal tip 16 of catheter 10. The amount of fluid pressure required to open the aspiration valve 24 is a function of the resiliency of the sleeve 30 material and its attachment to the catheter inner wall 19. The amount of fluid pressure required to open mouth 44 for fluid infusion is a function of the resiliency of the sleeve 30 material and the flexibility of jaws (or "lips") 48 and 48'.

Figure 3D:
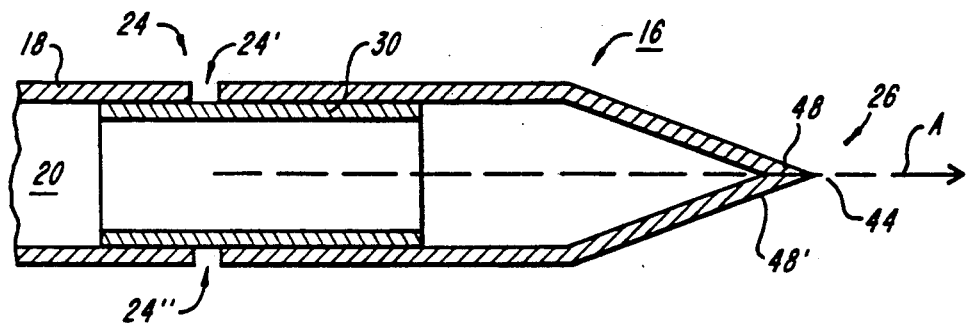
FIG. 3D shows an axial cross-section view of an alternative embodiment of the invention.
Figure 3E:
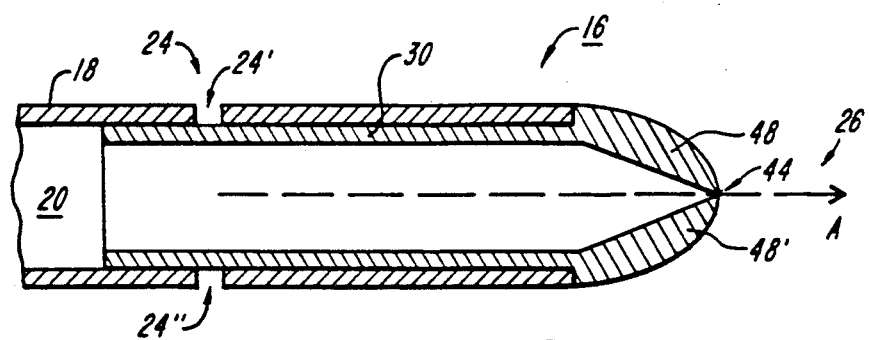
FIG. 3E shows an axial cross-section view of another alternative embodiment of the invention.
Figure 3F:
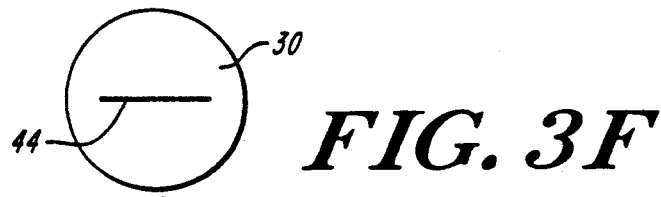
FIG. 3F shows an end view of the embodiment of FIG. 3E.

Infusion valve 26 may be alternatively formed in a variety of ways. For example, as shown in FIG. 3D, the tip of catheter distal end 16 may be terminated in nominally mated adjacent end flaps. In this form of the invention, the inner sleeve 30 extends only partway to the distal tip of the catheter. FIGS. 3E and 3F show another form of the invention in which the sleeve 30 ends with a slitted hemispherical portion, establishing the slit valve with lips 48 and 48'. Alternatively, valve 26 may be formed by tapering the distal end 16 of a circular cross-section catheter 10 down to an outer diameter less than the catheter nominal diameter, retaining a circular cross-section, wherein the cross-section of the interior of the catheter wall member 18 is constricted into a throat and down to a nominally closed mouth. Again valve 26 is nominally closed to fluid outflow and is effectively closed to fluid inflow. In any such embodiment, the mouth opens to fluid outflow when the fluid pressure inside of valve 26 is sufficiently higher than the fluid pressure outside of the mouth, to enable infusion of fluid into the patient.

It will now be further appreciated that in view of the simplicity of the present invention, a respective bidirectional check valve assembly as described above may be advantageously employed in each lumen of a multi-lumen catheter, so as to afford independent bi-directional control to each of the multiple lumens. The additional lumens may include bidirectional check valve assemblies of the type described above in conjunction with FIGS. 1-3C or those assemblies may be of a different type.

A preferred dual lumen catheter 10' in practice of the invention is shown in FIG. 4 having two valve assemblies 50, 60. The first bidirectional check valve assembly 50 controls a first lumen 52 of catheter 10'. Valve assembly 50 includes an aspiration valve 54 and an infusion valve 56. The second bidirectional check valve assembly 60 controls a second lumen 62 of the catheter and has an associated aspiration valve 64 and infusion valve 66. The operation of each of bidirectionally valved lumens 52 and 62 is substantially the same as that describe above in connection with FIGS. 3A-3C. This embodiment is shown in (inverted) perspective view in FIG. 5.

Figure 6A:
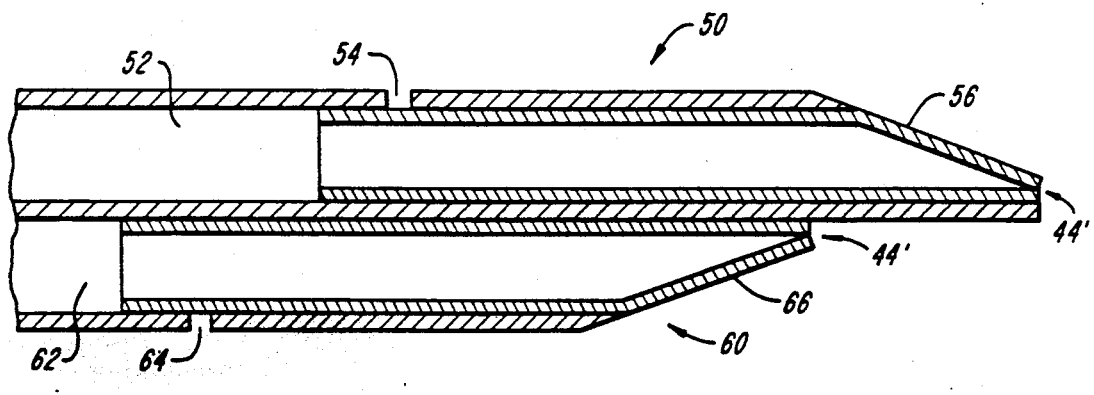
FIGS. 6A, 6B and 6C show axial cross-section views illustrating the operation of the dual lumen bidirectional check valve of the embodiment of FIGS. 4 and 5.
Figure 6B:
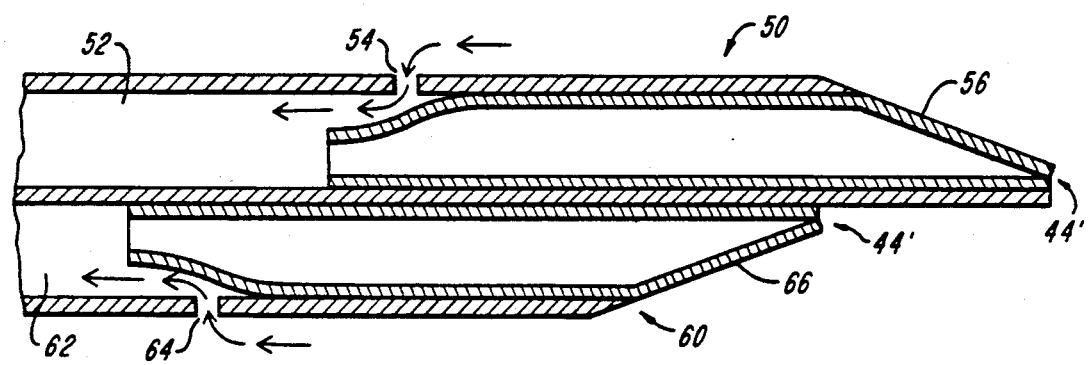
Figure 6C:
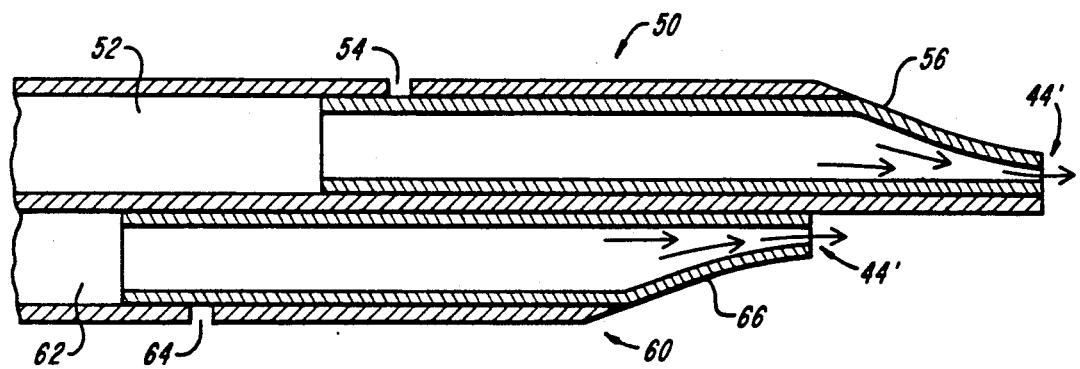

FIGS. 6A, 6B and 6C illustrate the operation of the dual lumen catheter of FIGS. 4 and 5. In FIG. 6A, there is little or no static pressure differential between each of the lumens 52, 62 and the region exterior to the catheter. Accordingly, both valves for each lumen are closed. In FIG. 6B, the static pressure in each of lumens 52, 62 is low enough to force the aspiration valves to open, establishing fluid flow into each of lumens 52, 62. In FIG. 6C, the static pressure in each of lumens 52, 62 is high enough to force the duck-billed infusion valves open, establishing fluid flow from each of lumens 52, 62 through the mouths 44'. Although in each of FIGS. 6A, 6B and 6C, the lumens are shown under similar static pressure conditions, the static pressure in each may alternatively be independently controlled.

As a result of the foregoing, an easily formed and installed bidirectional single lumen or multiple lumen catheter can be formed with two independent one way valves at the distal end of each lumen. The bidirectional valve assembly of the invention operates in three modes: (1) the nominally closed infusion valve opens only under positive pressure (i.e., the fluid in the catheter being pressurized to a level sufficiently above the bloodstream pressure to force the valve open for infusion of fluid to the patient); (2) the nominally closed aspiration valve opens only under negative pressure (i.e., the fluid pressure in the catheter is lower than that of the bloodstream by an amount sufficient to force the valves open for extraction of fluid from the patient's bloodstream); and (3) the valves are closed in all other cases.

Patency of the catheter is maintained merely by saline flush. Since blood does not backflow into the infusion valve, the risk of forming emboli in the valve and subsequently inadvertently pumping them into the bloodstream during fluid infusion is substantially reduced. Thus the need for heparinization of this valve is alleviated.

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A bidirectionally valved catheter comprising:

at least one elongated, flexible tubular element defining a lumen extending along an axis substantially parallel to the central axis of said tubular element and adapted for selective flow of fluid therein between a proximal end and a distal end of said tubular element, and a first bidirectional check valve assembly coupled to said lumen and disposed near said distal end of said tubular element, said valve assembly including an aspiration valve for fluid inflow from outside to inside said tubular element and an infusion valve for fluid outflow from inside to outside said tubular element, said aspiration valve including a sleeve valve positioned near said distal end, and said infusion valve including a slit valve at said distal end.

2. The catheter of claim 1 wherein said distal end terminates in a distal tip and wherein said aspiration valve comprises:

A. one or more inflow ports extending through the sidewall of said tubular element near said distal end and displaced from the distal tip of said catheter; and B. a flexible, tubular sleeve disposed within said tubular element and having an outer surface normally flush against the inner surface of said tubular element in the portion of said tubular element bearing said inflow ports, whereby substantially no fluid may flow through said inflow ports, and wherein a portion of said sleeve is displaceable to permit fluid inflow through said ports when the static pressure outside of said ports is higher than the static pressure inside said tubular element by an amount sufficient to force a portion of said sleeve away from the portion of said interior wall of said tubular element bearing at least one of said inflow ports, and wherein said infusion valve comprises:

a flexible valve section defining a tapered interior region contiguous to said lumen and extending from the tip of said distal end and terminating in a normally closed slit formed by opposed edges of said valve section whereby substantially no fluid may flow between said opposed edges, and wherein said opposed edges are displaceable in opposite directions to permit fluid outflow between said opposed edges when the static pressure inside said tapered interior region is higher than the static pressure outside said tip of said distal end by an amount sufficient to displace said opposed edges away from each other.

3. The catheter of claim 2 wherein said valve section is formed by an integral extension of the distal end of said tubular element.

4. The catheter of claim 2 wherein said valve section is formed by an integral extension of said sleeve.

5. The catheter of claim 2 wherein the cross-section of said distal end of said lumen is substantially circular.

6. The catheter of claim 2 wherein the cross-section of said distal end of said lumen is non-circular.

7. The catheter of claim 6 wherein said cross-section is substantially D-shaped.

8. The catheter of claim 2 wherein said valve assembly is nominally disposed to prevent fluid flow in the tubular element when there is substantially no fluid pressure differential across the infusion valve and the aspiration valve.

9. The catheter of claim 2 further comprising at least one additional lumen extending along an axis substantially parallel to said central axis wherein at least one of said additional lumens includes an additional bidirectional check valve assembly coupled thereto.

10. The catheter of claim 9 wherein said additional bidirectional check valve assembly is substantially similar to said first bidirectional check valve assembly.

11. A multiple lumen, bidirectionally valved catheter comprising:
an elongated flexible tubular element defining a plurality of lumens extending along axes substantially parallel to the central axis of said tubular element and adapted for selective flow of fluid therein between a proximal end and a distal end of said tubular element, and
a plurality of bidirectional check valve assemblies, each of said assemblies being associated with one of said lumens and including an aspiration valve for fluid inflow from outside said tubular element to inside said associated lumen and an infusion valve for fluid outflow from inside said associated lumen to outside said tubular element, and being coupled to said associated lumen and disposed near said distal end of said tubular element, wherein for one or more of said valve assemblies, said aspiration valve including a sleeve valve positioned near said distal end, and said infusion valve including a slit valve at said distal end.

12. The catheter of claim 11 wherein said distal end terminates in a distal tip and wherein said aspiration valve comprises:
A. one or more inflow ports extending through the sidewall of said tubular element to its associated lumen near said distal end and displaced from the distal tip of said catheter; and
B. a flexible, tubular sleeve disposed within said tubular element and having an outer surface normally flush against the inner surface of said its associated lumen of said tubular element in the portion of said tubular element bearing said inflow ports whereby substantially no fluid may flow through said inflow ports, and wherein a portion of said sleeve is displaceable to permit fluid inflow through said ports when the static pressure outside of said ports is higher than the static pressure inside said tubular element by an amount sufficient to force a portion of said sleeve away from the portion of said interior wall of said tubular element bearing at least one of said inflow ports, and said infusion valve comprises:
a flexible valve section defining a tapered interior region contiguous to its associated lumen and extending from the tip of said distal end and terminating in a normally closed slit formed by opposed edges of said valve section whereby substantially no fluid may flow between said opposed edges, and wherein said opposed edges are displaceable in opposite directions to permit fluid outflow between said opposed edges when the static pressure inside said tapered interior region is higher than the static pressure outside said tip of said distal end by an amount sufficient to displace said opposed edges away from each other.

* * * * *